United States Patent

Mattes et al.

Patent Number: 5,183,813
Date of Patent: Feb. 2, 1993

[54] ANTIARRHYTHMIC AGENTS

[75] Inventors: Kenneth C. Mattes, Rochester; Bhaskar R. Venepalli, Fairport, both of N.Y.

[73] Assignee: Sterling Winthrop Inc., New York, N.Y.

[21] Appl. No.: 838,391

[22] Filed: Feb. 19, 1992

[51] Int. Cl.⁵ .................. A61K 31/52; A61K 31/415
[52] U.S. Cl. .................................. 514/150; 514/394; 534/778; 534/787; 548/302.1; 548/309.7
[58] Field of Search ................. 548/330, 326; 514/394, 514/150; 534/778, 787

[56] References Cited

U.S. PATENT DOCUMENTS

| | | | |
|---|---|---|---|
| 3,962,256 | 6/1976 | Fauran et al. | 546/199 |
| 4,513,973 | 4/1985 | Sinclair | 273/237 |
| 4,581,329 | 4/1986 | Sugimoto et al. | 430/567 |
| 4,581,370 | 4/1986 | Diamond et al. | 514/399 |
| 4,804,662 | 2/1989 | Nicklisch et al. | 514/252 |
| 4,880,804 | 11/1989 | Carini et al. | 514/234.5 |
| 4,952,485 | 8/1990 | Shibahara et al. | 430/502 |

Primary Examiner—Mary C. Lee
Assistant Examiner—Lenora Ava Miltenberger
Attorney, Agent, or Firm—William J. Davis

[57] ABSTRACT

A pharmaceutical composition for treating cardiac arrhythmias or inhibiting ventricular tachycardias comprises an effective amount of a compound having the structural formula:

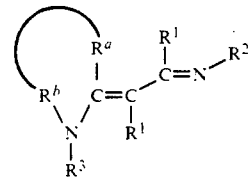

or a pharmaceutically acceptable salt thereof;
wherein at least one $R^1$ is H and the other $R^1$ is H, alkyl, halogen, alkoxy or alkylthio;
$R^2$ is alkyl containing at least 2 carbon atoms, benzyl or aryl;
$R^3$ is alkyl or aryl; and
$R^a$ and $R^b$ taken together with the carbon and nitrogen atoms to which they are attached represent a heterocyclic group; together with a non-toxic pharmaceutically acceptable carrier. The compounds and compositions are useful in methods of treating cardiac arrhythmias and inhibiting ventricular tachycardias in mammalian subjects.

In composition of matter aspect, this invention relates to certain novel 2-(2-iminoethylidene)benzimidazolines and neutral tautomers thereof.

1 Claim, No Drawings

ANTIARRHYTHMIC AGENTS

FIELD OF THE INVENTION

This invention relates to antiarrhythmic pharmaceutical compositions comprising compounds containing a nitrogen-containing group connected via an ethanediylidene group to an imino group, and pharmaceutically acceptable salts of such compounds, and pharmaceutical methods using such compositions. This invention further relates to certain novel 2-(2-iminoethylidene)benzimidazolines.

BACKGROUND OF THE INVENTION

Cardiac arrhythmia, a frequent problem in many patients, particularly those suffering from myocardial infarction, as well as anesthetized patients and patients under treatment with digitalis, a cardiac tonic, is a variation from the normal rhythm of the heart beat and includes sinus arrhythmia, premature beat, heart block, atrial fibrillation, atrial flutter, pulsus alternans, and paroxysmal tachycardia. Cardiac contractions (heart beats) are initiated by electrical impulses originating in the sinoatrial node of the heart at regular intervals, generally about 60–100 beats per minute. The impulses rapidly spread by conduction to all parts of the ventricles stimulating synchronous contractions of all ventricular muscle. Arrhythmias occur as a result of any abnormality in this rhythmic process, for example, in the site of origin of the impulse, its regularity, strength, and its conduction. An excellent discussion of the mechanisms involved, including the sodium, potassium, and calcium channeling effects which occur, and the cardiac effects of current medications, particularly sodium channel-blocking drugs such as quinidine, procainamide, and lidocaine is provided by Luc M. Hondeghem and Jay W. Mason in Chapter 13, "Agents Used In Cardiac Arrhythmias" of the Lange Medical Book, Basic and Clinical Pharmacology, Third Edition, Edited by Bertram G. Katzung, Appleton and Lange, Norwalk, Conn./Los Altos, Calif., page 151.

U.S. Pat. No. 4,581,370 describes certain imidazolium salts which are useful as antiarrhythmic agents. U.S. Pat. No. 4,804,662 describes 4-[1H-imidazol-1-yl] benzamides and their use in the treatment of cardiac arrhythmias. However, these patents do not suggest the pharmaceutical compositions of the present invention comprising a compound having a nitrogen containing group connected via an ethanediylidene group to an imino group.

SUMMARY OF THE INVENTION

We have discovered that compounds containing a nitrogen containing group connected via an ethanediylidene group to an imino group, and pharmaceutically acceptable salts of such compounds, are useful as Class I and Class III antiarrhythmic agents. The compounds are capable of protonation to form the corresponding amidinium ion system with resonance of the resulting structure and deprotonation of the imino hydrogen to produce an uncharged structure.

More particularly, in accordance with this invention, there is provided a pharmaceutical composition for treating cardiac arrythmias or inhibiting ventricular tachycardias comprising an effective amount of a compound having the formula:

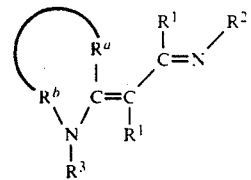

and pharmaceutically acceptable salts of such compound;
wherein at least one $R^{1'}$ is H and the other $R^1$ is H, alkyl, halogen, alkoxy or alkylthio;
$R^2$ is alkyl containing at least 2 carbon atoms, benzyl or aryl;
$R^3$ is alkyl or aryl; and
$R^a$ and $R^b$ taken together with the carbon and nitrogen atoms to which they are attached represent a heterocyclic group; together with a pharmaceutically acceptable carrier.

In another embodiment of the invention, there is provided a method for treating arrhythmias or inhibiting ventricular tachycardias in a mammalian subject in need thereof comprising administering to the subject an effective amount of the above-described compound.

In another aspect, this invention relates to novel 2-(2-iminoethylidene)benzimidazolines preferably having the structural formula:

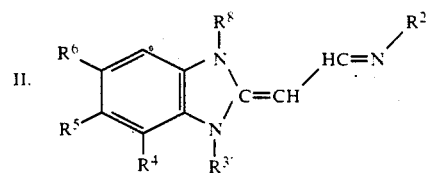

wherein
$R^{2'}$ is t-butyl or phenyl;
$R^{3'}$ is ethyl or 2,2,2,-trifluoroethyl;
$R^4$, $R^5$, and $R^6$ are independently H, alkyl, aryl, alkylsulfonamido, arylsulfonamido, alkoxy, aryloxy, alkylthio, an ester group, an amide group, arylazo, alkenyl, cyano, halo, nitro, acyl, or $R^4$ and $R^5$, or $R^5$ and $R^6$, or $R^4$, $R^5$ and $R^6$ taken together represent the atoms necessary to complete a fused carbocyclic or heterocyclic ring group;
and $R^8$ is alkyl or aryl.
Such compounds can be in their charged ionic form or in the above-depicted neutral protonated form.

DESCRIPTION OF THE PREFERRED EMBODIMENTS

The pharmaceutical compositions of this invention comprise an agent containing a nitrogen containing group linked to an imino group through an ethanediylidene group. Preferred antiarrythmic agents are compounds having the structural Formula I set forth in the summary above.

In structural Formula I above, at least one $R^1$ is H and the other $R^1$ is H; halogen, such as chloro, bromo or iodo; alkyl, preferably containing from 1 to 4 carbon atoms such as methyl, ethyl, propyl or butyl; alkoxy, the alkyl portion of which preferably contains from 1 to 4 carbon atoms such as methoxy, ethoxy, propoxy or butoxy; or alkylthio, the alkyl portion of which preferably contains from 1 to 4 carbon atoms such as methylthio, ethylthio, propylthio, and the like.

$R^2$ is substituted or unsubstituted alkyl preferably containing from 2 to about 15 carbon atoms such as ethyl, propyl, t-butyl, hexyl and the like; benzyl; or substituted or unsubstituted aryl containing from 6 to about 16 carbon atoms such as phenyl or naphthyl. The alkyl and aryl groups can be unsubstituted or substituted with inert, nonionic substituents such as halogen, such as described for $R^1$ above; alkyl, preferably containing from 1 to 6 carbon atoms such as methyl, ethyl and propyl; or aryl, preferably containing from 6 to 10 carbon atoms such as phenyl or naphthyl. Exemplary $R^2$ groups include benzyl, tolyl and xylyl. Particularly preferred $R^2$ groups include phenyl, benzyl, and t-butyl.

$R^3$ is a nonionic group selected from substituted or unsubstituted alkyl preferably containing from 1 to about 4 carbon atoms such as methyl, ethyl, propyl or butyl; or substituted or unsubstituted aryl preferably containing from 6 to about 10 carbon atoms such as phenyl or naphthyl. The alkyl and aryl groups can be unsubstituted or substituted with inert, nonionic substituents such as halogen, such as chloro, bromo, iodo and fluoro, and alkyl such as described for $R^1$ above. Exemplary $R^3$ groups include cyanomethyl, methoxyethyl, bromopropyl, and 2,2,2-trifluoro-1-ethyl.

$R^a$ and $R^b$ taken together with the carbon and nitrogen atoms to which they are attached preferably represent a substituted or unsubstituted heterocyclic group as hereinafter described. The heterocyclic group comprises at least one nitrogen-containing ring capable of forming an amidinium ion. The amidinium ion-containing ring preferably contains 5 or 6 ring atoms. The amidinium ion-containing ring can contain one or more additional heteroatoms, such as nitrogen, oxygen or sulfur atoms in the ring. The heterocyclic group includes the amidinium ion-containing ring and optionally from 1 to 4 fused carbocyclic or heterocyclic ring groups, each ring preferably containing from 5 to 7 ring nuclear carbon and heteroatoms such as N, O or S. Exemplary fused rings include benzene, naphthalene,

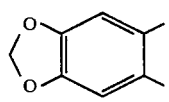

and

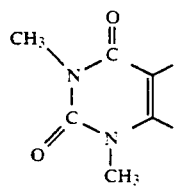

$R^a$ and $R^b$ taken together preferably represent a group having the structural formula:

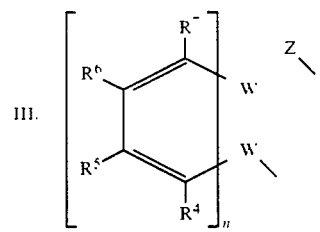

In formula III above,

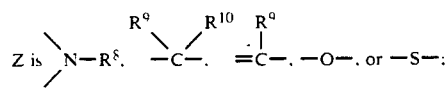

wherein $R^8$ is substituted or unsubstituted alkyl, preferably containing from 1 to 8 carbon atoms such as methyl or ethyl; or substituted or unsubstituted aryl preferably containing from 6 to 10 carbon atoms such as phenyl. Such alkyl and aryl groups can be unsubstituted or substituted with inert, nonionic substituents such as halogen and alkyl as described for $R^3$ above. Preferred $R^8$ groups include methyl, ethyl, trifluoromethyl, trifluoroethyl, t-butyl, phenyl, p-chlorophenyl, or benzyl. $R^9$ and $R^{10}$ are independently H or alkyl, preferably containing from 1 to 4 carbon atoms such as methyl, ethyl, propyl or butyl. When Z is —S—, it is preferred that alkyl substituents be present for one or more of $R^3$, $R^4$, $R^5$, $R^6$, $R^7$, $R^{5'}$, $R^{6'}$ and both $R^{5''}$ so that such alkyl substituents together contain greater than 2 carbon atoms.

Each W in Formula III above is

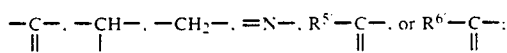

and n is 0 or 1. When n is 1, the total group

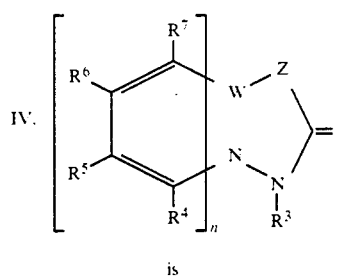

is

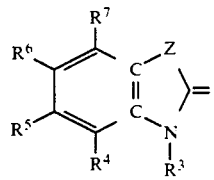

wherein $R^3$ and Z are as described above;

$R^4$, $R^5$, $R^6$ and $R^7$ independently can be H; substituted or unsubstituted alkyl, preferably containing from 1 to about 16 carbon atoms such as methyl, ethyl, i-propyl, hexyl, decyl, and the like, such alkyl group optionally being terminated with or interrupted by one or more hetero atoms or hetero atom-containing groups such as ester, amide, oxy, thio, sulfonyl, and the like; substituted or unsubstituted aryl, preferably containing from 6 to about 16 carbon atoms such as phenyl or naphthyl; substituted or unsubstituted alkylsulfonamido, the alkyl portion of which preferably contains from 1 to 10 carbon atoms; substituted or unsubstituted arylsulfonamido, the aryl portion of which preferably contains from 6 to 10 carbon atoms; alkoxy, the alkyl portion of which preferably contains from 1 to 10 carbon atoms, such as methoxy and propoxy; aryloxy, the aryl portion of which preferably contains from 6 to 10 carbon atoms; alkylthio, the alkyl portion of which preferably contains from 1 to 10 carbon atoms, such as methylthio and ethylthio; arylthio, the aryl portion of which preferably contains from 6 to 10 carbon atoms; an ester group, e.g., a group represented by

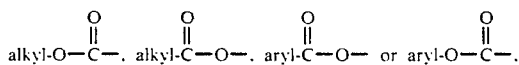

the alkyl and aryl portions of which preferably contain from 1 to 10 carbon atoms; an amide group, e.g., alkylcarbonylimino, alkyliminocarbonyl, arylcarbonylimino and aryliminocarbonyl, the alkyl and aryl portions of which preferably contain from 1 to 10 carbon atoms; arylazo, the aryl portion of which preferably contains from 6 to 10 carbon atoms; alkenyl, preferably containing from 2 to 16 carbon atoms, such alkenyl group optionally being terminated with or interrupted by one or more heteroatoms or heteroatom-containing groups such as ester, amide, oxy, thio, sulfonyl, and the like; cyano; halo, such as chloro, bromo, fluoro or iodo; nitro; acyl, e.g.,

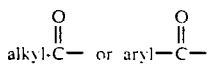

containing 2 to about 10 carbon atoms, the alkyl and aryl portions of which preferably can be unsubstituted or substituted; or $R^4$ and $R^5$, or $R^5$ and $R^6$, or $R^6$ and $R^7$, or $R^4$, $R^5$, $R^6$, or $R^5$, $R^6$ and $R^7$ taken together with the carbon atoms to which they are attached represent the atoms necessary to complete a monocyclic or polycyclic aromatic, carbocyclic or heterocyclic fused ring group preferably containing from 1 to 3 rings, each ring preferably containing from 5 to 7 ring nuclear carbon and heteroatoms such as N, O or S. Exemplary fused ring groups include benzene, naphthalene and

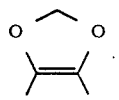

The $R^4$, $R^5$, $R^6$ and $R^7$ groups can be unsubstituted or substituted with inert, nonionic substituents such as described for $R^2$ above. Exemplary $R^4$, $R^5$, $R^6$ and $R^7$ groups include methoxyethyl, acetoxyethyl, sulfamoyl-phenyl, methylsulfonyl, phenylsulfonyl, ethoxycarbonyl, phenoxycarbonyl, methylcarbonylimino, N-phenylcarbamoyl, phenylazo, butenyl, acetyl, propionyl, benzoyl, benzo, naphtho and the like. When n is 1, it is preferred that $R^3$ is other than aryl or aralkyl.

When n is 0, the total group IV above is

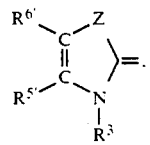

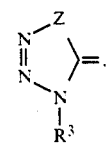

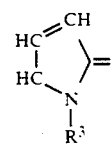

or

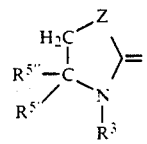

wherein $R^3$ and Z are as defined above;

each $R^{5'}$ and $R^{6'}$ are independently H, alkyl, aryl, alkylsulfonamido, arylsulfonamido, alkoxy, aryloxy, alkylthio, arylthio,

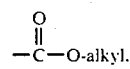

amide, arylazo, alkenyl, cyano, halo, nitro or acyl, as defined for $R^5$ and $R^6$ above; and each $R^{5''}$ is independently H, aryl or alkyl as defined for $R^5$ and $R^6$ above. When n is 0 and any of $R^{5'}$, $R^{6'}$ or $R^{5''}$ is aryl, it is preferred that $R^3$ is other than aryl or aralkyl.

It is preferred that the above-described compounds be free of electronegative substituents such as $-NO_2$, $-SO_2$ and $-SO_3-$ groups when used in the pharmaceutical compositions of this invention. If such groups are present, it is preferred that they be distant from the pharmacophore.

In the practice of this invention, the above-described compounds can be used in either their charged (ionic) salt or uncharged (neutral) form. The salt can be formed by protonation of the uncharged neutral form with an appropriate acid as indicated below:

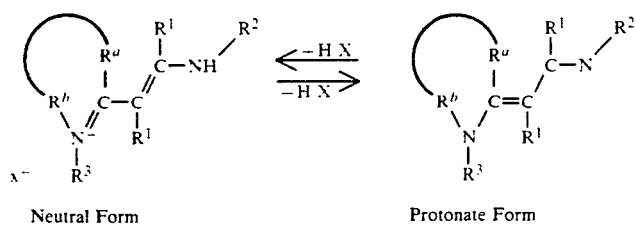

Neutral Form        Protonate Form

The acid addition salt (protonate) form and neutral forms are considered to be tautomers as such term is used herein. It is understood that one and/or both forms are useful in the pharmaceutical compositions of this invention.

In the protonate form, x- is an acid anion such as chloride, bormide, iodide, methosulfate, p-toluenesulfonate, trifluoromethanesulfonate, tetrafluoroborate, perchlorate and the like.

The following are specific examples of agents useful in the practice of this invention.

-continued

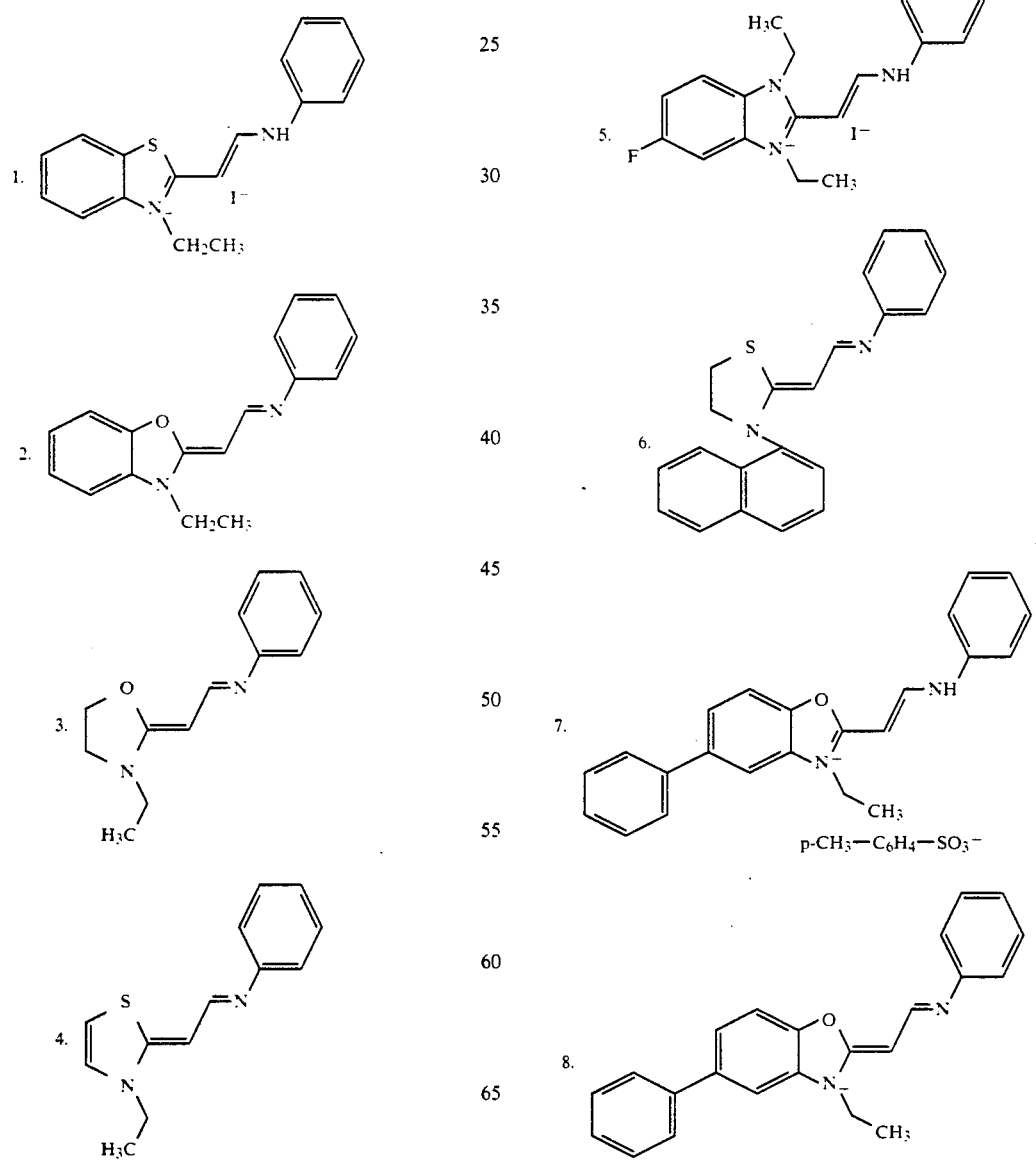

-continued
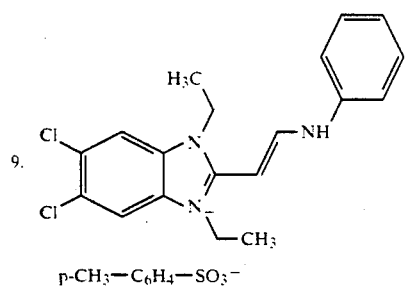
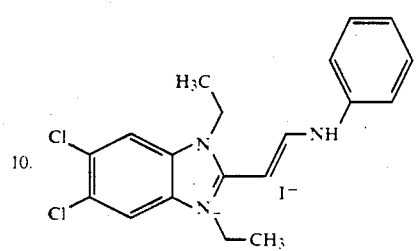
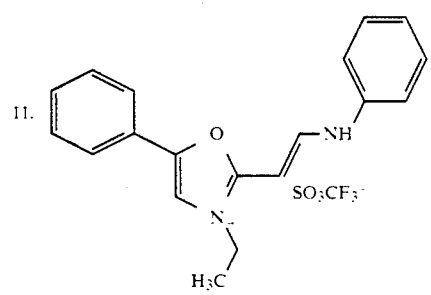
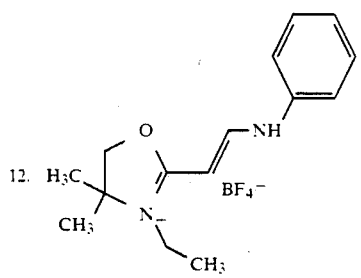
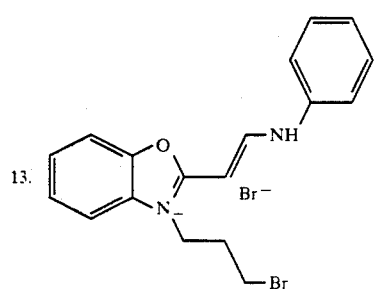
-continued
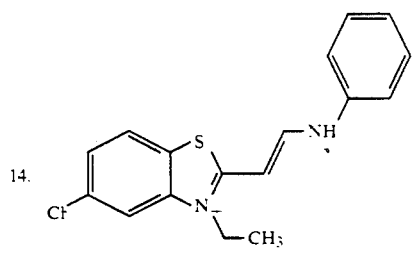
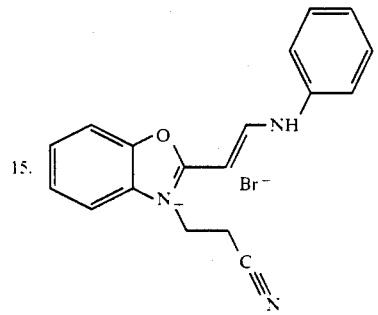
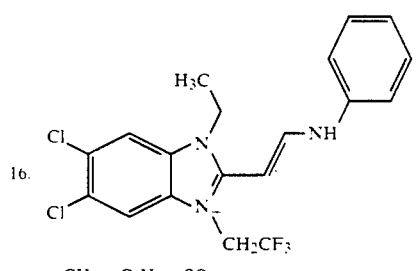
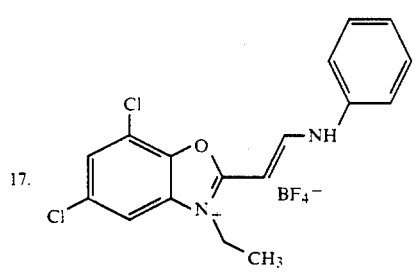
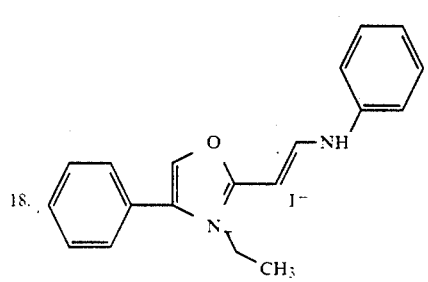

-continued
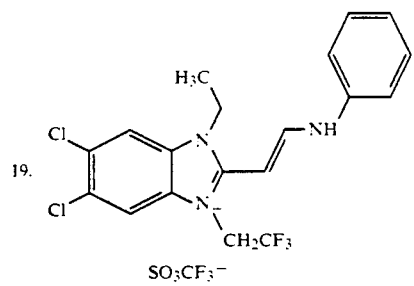
19.
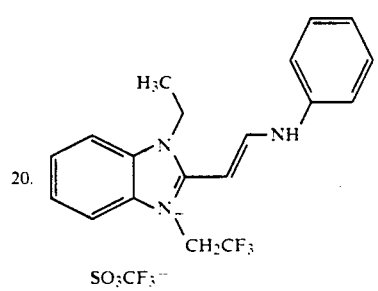
20.
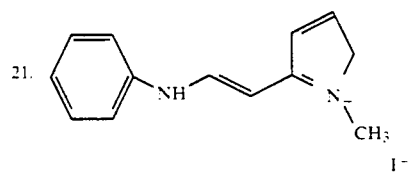
21.
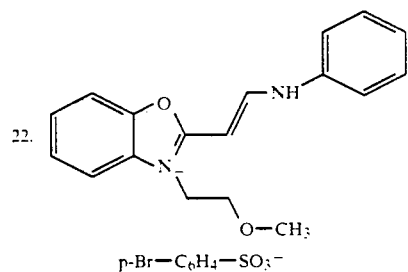
22.
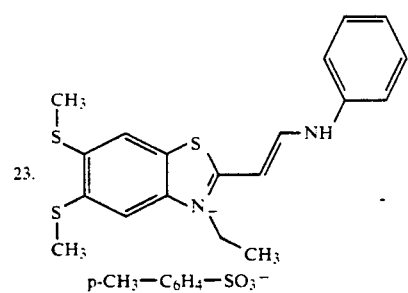
23.
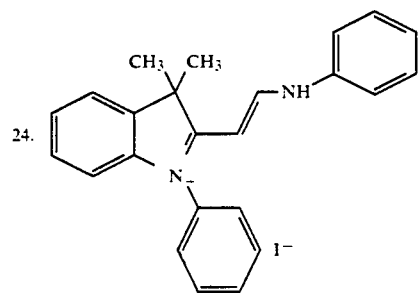
24.
-continued
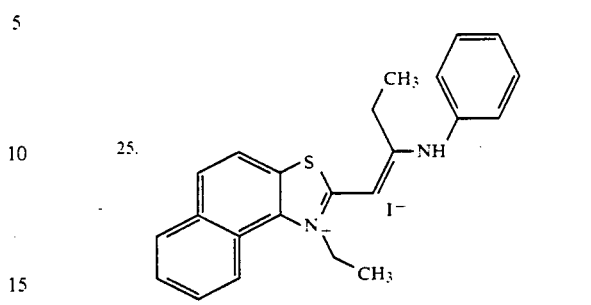
25.
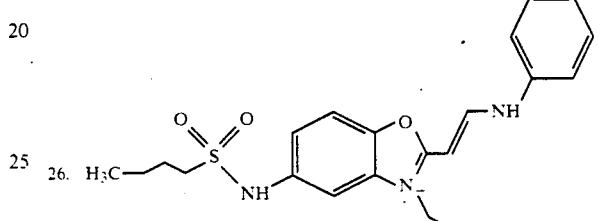
26.
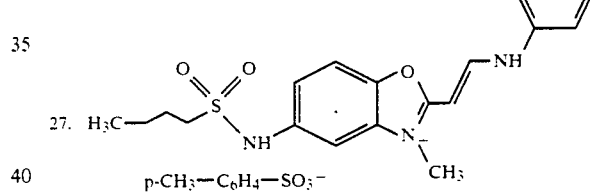
27.
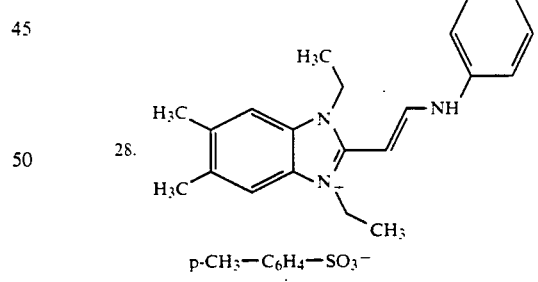
28.
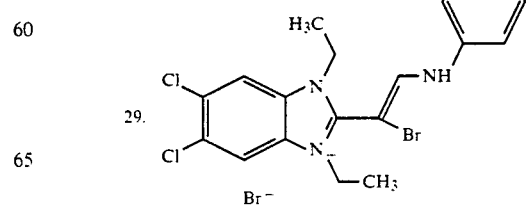
29.

-continued
30. 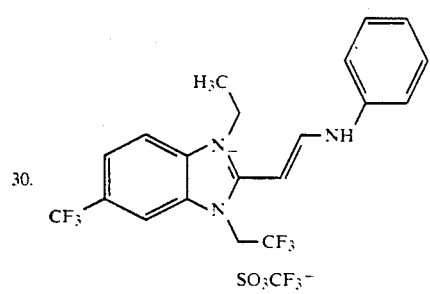
31. 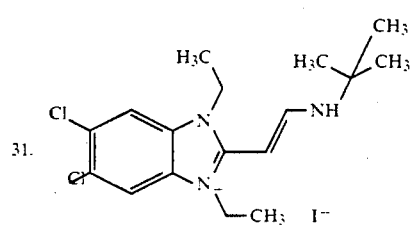
32. 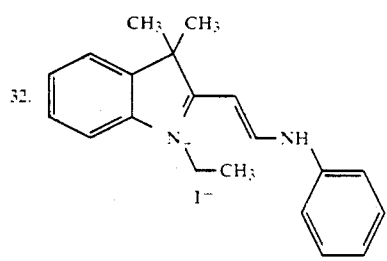
33. 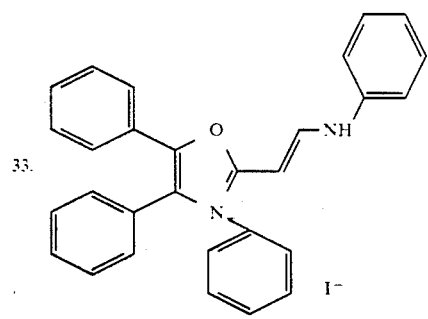
34. 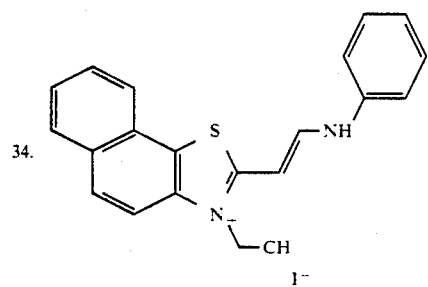
-continued
35. 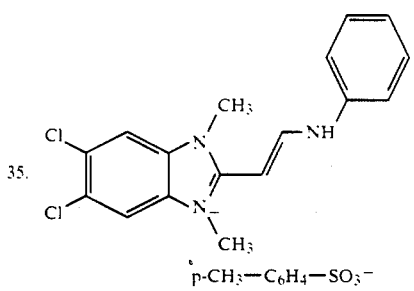
36. 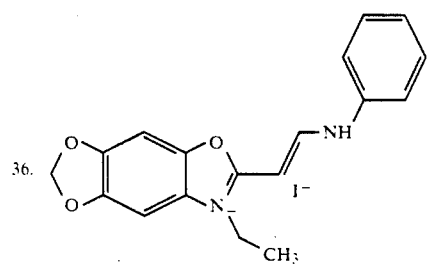
37. 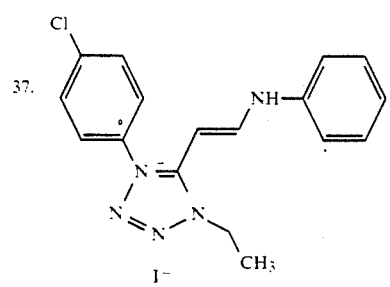
38. 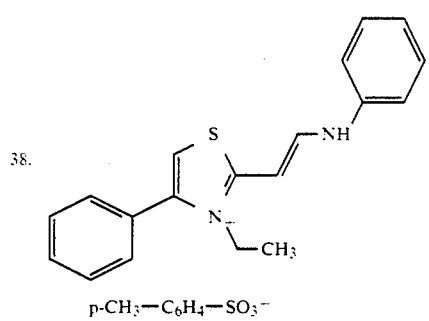
39. 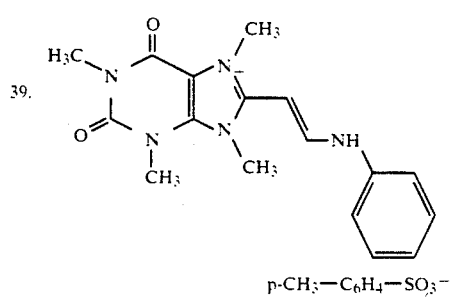

-continued

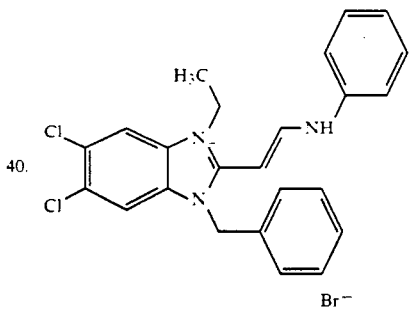

40.

This invention also provides various novel 2-(2-iminoethylidene)-3-substituted-benzimidazolines. Such compounds preferably have the structural formula:

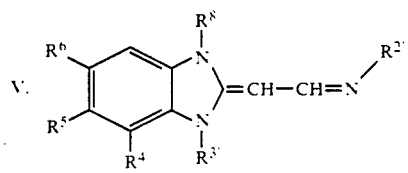

V.

p1 wherein $R^{2'}$ is t-butyl or phenyl;

$R^{3'}$ is ethyl or 2,2,2-trifluoroethyl; and $R^4$, $R^5$, $R^6$ and $R^8$ are as defined above.

A particularly preferred class of compounds has the structural formula V above wherein $R^4$ is H and $R^5$ and $R^6$ are H or halogen. Preferred examples of this class of compounds include compounds 5, 9, 10, 16, 19, 20, and 31 set forth above.

The compounds useful in the practice of this invention can be prepared by techniques known to those skilled in the art, for example, by reacting a 2-methyl-heterocyclic onium salt with an alkyl isoformanilide. This synthetic route is illustrated in the following Preparation 1.

Alternatively, the compounds useful in the practice of this invention can be prepared by condensing a 2-vinylheterocyclic onium salt having a reactive negative substituent on the 2-position of the vinyl group with a primary amine. The reactive negative substituent can be, e.g., a halo, cyano, alkylthio, arylthio, alkoxy, anilino or acetanilido group. Preferred examples of the amine include aniline, t-butylamine, and benzylamine. Details of the preparation procedures are set forth in the examples which follow. The procedures are similar to those set forth by T. Ogata, Proc. Imp. Acad. (Tokyo), Vol. 13, page 325 (1937) and F. L. White and G. H. Keyes, U.S. Pat. No. 2,166,736, the disclosures of which are hereby incorporated by reference. These references also disclose the preparation of 2-(2-substituted-vinyl) heterocyclic onium salts useful as starting materials.

The compositions of this invention display Class I and Class III antiarrhythmic activity. In 1970 Vaughan Williams devised the now well known method for classifying various antiarrhythmic agents. Briefly, Class I agents, typified, for example, by flecainide, lidocaine or mexiletine are local anesthetics on nerve and myocardial membranes which slow conduction, thereby decreasing the propagation of ectopic beats and suppressing the tendency of damaged cells to initiate ectopic beats. The Class II agents are the so-called β-blockers exemplified by propanolol. The Class III agents represented by bretylium or amiodarone prolong the action potential duration of the heart cells thus increasing the time interval in which the heart cells are unexcitable (refractory period) without slowing conduction or changing the excitability of the cardiac cells.

It has been found that the above-described compounds bind to the $\alpha_2$ adrenergic receptor. Consequently, in addition to their utility as antiarrhythmic agents, these compounds are also expected to be useful as $\alpha_2$ adrenergic binding inhibitors. Furthermore, the compounds are effective in inhibiting ventricular tachycardias.

The pharmaceutical compositions of the present invention include one or more of the above-described compounds formulated into compositions together with one or more nontoxic physiologically acceptable carriers, adjuvants, diluents, or vehicles which are collectively referred to herein as carriers, for parenteral injection, for oral administration in solid or liquid form, for rectal or topical administration, and the like.

The compositions can be administered to humans and animals either orally, rectally or parenterally (intravenously, intramuscularly or subcutaneously).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, saline, buffered aqueous solutions, ethanol, polyols (propylene glycol, polyethyleneglycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. A typical formulation suited to intravenous or intramuscular administration can contain one of the above-described compounds in the amount of about 50 to 150 mg and optionally a solubilizing agent and sufficient sterile water to bring the volume to about 5–100 ml. Such formulation can be infused at a constant rate or injected one to four times per day or more often depending upon the particular condition of the subject treated.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption; for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, such as, for example, starches, lactose, sucrose, glucose, mannitol, calcium sulfate, sodium benzoate, and silicic acid, (b) binders, such as, for example, cellulose, carboxymethylcellulose, alginates, gelatin, polyvinylpyrrolidone, sucrose and acacia, (c) humectants, such as, for example, glycerol, (d) disintegrating agents, such as, for example, agar-agar, calcium carbonate, potato or tapioca starch, alginic acid, certain complex silicates and sodium carbonate, (e) solution retarders, such as, for example, paraffin, (f) absorption accelerators, such as, for example, quaternary ammonium compounds, (g) wetting agents, such as, for example, cetyl alcohol and glycerol monostearate, (h) adsorbents, such as, for example, kaolin and bentonite, and (i) lubricants, such as, for example, talc, calcium stearate, magnesium stearate, solid polyethylene glycols, sodium lauryl sulfate or mixtures thereof. In the case of capsules, tablets and pills, the dosage forms may also comprise buffering agents.

Such formulations can be compressed into tablets or can be encapsulated into gelatin for oral administration. The capsule can contain one of the above-described compounds in an amount of about 1 to about 500 mg. Such formulations can be administered orally at the dose of about 1 to 4 capsules per day or more often as needed depending on the particular condition and subject treated.

Compounds useful in the practice of this invention preferably exhibit a solubility in the carrier, e.g., a saline solution, of at least about 3 mg/mL and more preferably of at least 5 mg/mL up to 10 mg/mL and greater.

The pharmaceutical compositions of this invention optionally can contain one or more other pharmaceutically active substances.

The following examples further illustrate the invention:

EXAMPLES

Preparation of
2-(2-Anilinovinyl)-5,6-dichloro-1-ethyl-3-(2,2,2-trifluoroethyl)benzimidazolium p-toluenesulfonate

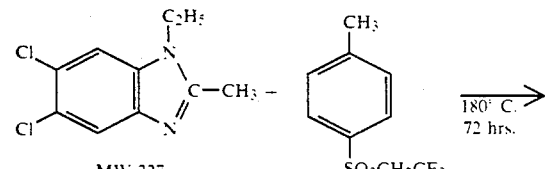

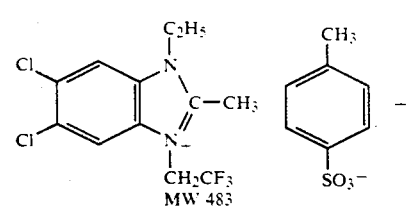

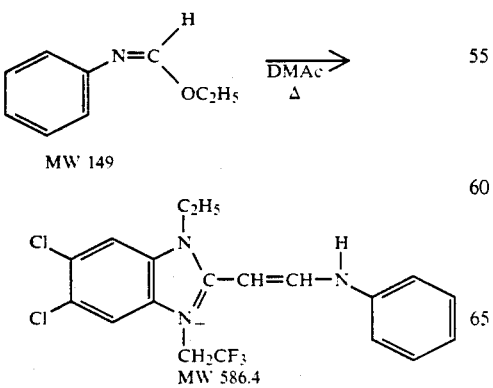

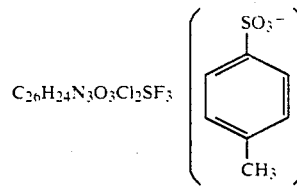

A mixture of 50 g (0.197 mole) of 2,2,2-trifluoroethyl p-toluenesulfonate and 40 g (0.175 mole) of 5,6-dichloro-1-ethyl-2-methylbenzimidazole were place in a 250 mL single-neck flask fitted with a condenser and placed in an oil bath and heated to 160° C. for 24 hr, then heated at 180° C. for another 48 hr, removed from the oil bath and allowed to cool. The thick, hard material was dissolved in about 20 mL of methanol and the solution was poured into 1 L of diethyl ether. A tan solid precipitated which was collected by filtration, washed in diethyl ether, and dried. Yield 63 g (74.5%), mp 208°–210° C. The solid product, 5,6-dichloro-1-ethyl-2-methyl-3-(2,2,2 trifluoroethyl)benzimidazolium p-toluenesulfonate, was washed again in a small amount of methyl ethyl ketone, collected by filtration and dried again. The melting point increased to 216° C.

A slurry of 30 g (0.062 mole) of the 5,6-dichloro-1-ethyl-2-methyl-3-(2,2,2-trifluoroethyl)benzimidazolium p-toluenesulfonate in 150 mL of N,N-dimethylacetamide was treated with 45 g (about 0.3 mole, a large excess) of ethyl iso-formanilide, i.e., N-(ethoxymethylene)aniline, the mixture stirred and heated to 150° C., allowed to cool to 120° C. where it was maintained for 5 minutes, and then allowed to cool slowly to 30° C. The solution was poured into 1.5 L of cyclohexane, stirred, allowed to settle, and the dark reddish oil was separated. The oil was washed with another 500 mL of cyclohexane, separated, treated with 200 mL of methyl ethyl ketone, warmed to a uniform solution and cooled in a freezer to produce a bright yellow-orange solid. The solid was collected by filtration, washed with cold methy ethyl ketone, and dried to produce 23 g melting at 215°–217° C. The mass spec. and NMR spec. are consistent with the assigned structure.

Preparation of
2-(2-t-Butylaminovinyl)-5,6-dichloro-1,3-diethylbenzimidazolium Iodide

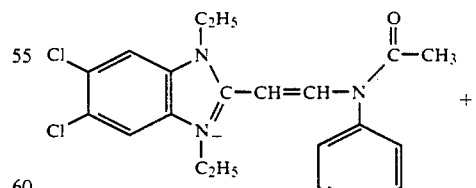

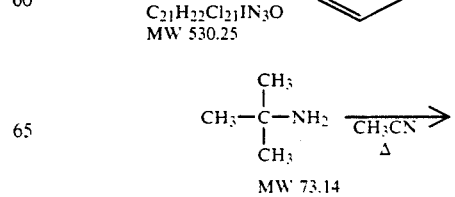

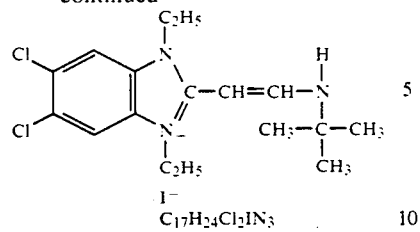

$C_{17}H_{24}Cl_2IN_3$

A 5.3 g (0.01 mole) sample of 2-(2-acetanilidovinyl)-5,6-dichloro-1,3-diethylbenzimidazolium iodide was dissolved in 100 mL of acetonitrile by warming and stirring in a 250 mL beaker. At about 50° C., 3 mL of t-butylamine was added and the resulting reddish mixture was stirred for 10 minutes and then concentrated to a thick oil in a rotary evaporator. The oil was diluted with diethyl ether, and crystallized by scratching the flask with a glass rod. The crystals were collected, reslurried with diethyl ether, collected again, and dried. The procedures were repeated and the product of both runs combined to yield 8 g melting at 220°-222° C. (shrinkage at 216° C.). The mass spectrum and NMR were consistent with the assigned structure.

Pharmaceutical Activity

The compounds of this invention were evaluated by the following Aconitine Infusion Test for Assessing Antiarrhythmic Activity [literature reference: P. U. Nwangwu, S. J. Holslaw, and S. J. Stohs. Arch. Int. Pharmacodyn., 229, 219-226 (1977)]. Each test was run on three male mice in separate runs:

Male mice weighing 19-25 grams each are anesthetized with sodium pentobarbital (60 mg/kg. i.p.). Needle electrodes were appropriately placed to record the electrocardiogram and a control tracing made using a conventional electronic lead II electrocardiograph machine. Five minutes later, the test compound was injected at the concentration noted, intravenously. Three minutes after intravenous administration of test compound, aconitine solution (5 mcg/mL) was injected via the tail vein at a precise rate of 0.25 mL/min with a Model 355 Sage infusion pump. The time in seconds to the onset of the initial arrhythmia (first discernible sign of persistent, more than 5 seconds, deviation from normal sinus rhythm) as well as the time to the onset of ventricular tachycardia were determined from the EKG. Increase in both parameters by more than 50% (>50) denotes substantial antiarrhythmic activity.

The results for compounds useful in the practice of this invention are recorded below. The data recorded are the percent increases in time of onset of arrhythmic and onset of ventricular tachycardia, respectively, above the normal, i.e., after aconitine treatment without drug. The control employed is Yohimbine hydrochloride, an adrenergic blocking agent as well as Lidicaine and Quinidine.

Antiarrhythmia Test Results for Compounds of the Invention

| Example | Dose (mg/kg) | Initial Arrhythmia | Ventricular Tachycardia |
|---|---|---|---|
| 1 | 100 | 60 | 63 |
| 1 | 100 | 56 | 63 |
|  | 50 | 38 | 17 |
| 1 | 100 | 56 | 63 |
| rerun | 100 | 60 | 63 |
|  | 50 | 38 | 17 |
| 2 | 100 | 64 | 59 |
|  | 100 | 56 | 67 |
|  | 50 | 29 | 26 |
| 3 | 100 | 122 | 77 |
|  | 50 | 63 | 59 |
|  | 25 | 2 | 5 |
| 4 | 100 | Died | Died |
|  | 50 | 177 | 105 |
|  | 25 | 92 | 59 |
|  | 10 | 2 | 0 |
| 5 | 100 | 116 | 101 |
|  | 50 | 89 | 77 |
|  | 25 | 45 | 32 |
| 6 | 100 | 177 | 105 |
|  | 50 | 133 | 94 |
|  | 25 | 0 | 0 |
| 7 | 100 | 111 | 98 |
|  | 50 | 102 | 71 |
|  | 25 | 40 | 28 |
| 8 | 100 | 97 | 79 |
|  | 50 | 61 | 64 |
|  | 25 | 21 | 15 |
| 9 | 100 | 88 | 66 |
|  | 100 | 76 | 53 |
|  | 50 | 36 | 35 |
| 10 | 100 | 82 | 68 |
|  | 100 | 78 | 62 |
|  | 50 | 8 | 0 |
| 10 rerun | 100 | 79 | 62 |
|  | 100 | 82 | 68 |
|  | 50 | 32 | 30 |
| 11 | 100 | 150 | 120 |
|  | 50 | 101 | 98 |
|  | 25 | 7 | 22 |
| 12 | 100 | 159 | 112 |
|  | 50 | 107 | 68 |
|  | 25 | 25 | 21 |
| 13 | 100 | Died | Died |
|  | 50 | 93 | 72 |
|  | 25 | 66 | 55 |
|  | 10 | 2 | 0 |
| 14 | 100 | 75 | 58 |
|  | 100 | 73 | 52 |
|  | 50 | 30 | 20 |
| 15 | 100 | Died | Died |
|  | 50 | 77 | 76 |
|  | 50 | 68 | 62 |
|  | 25 | 26 | 45 |
| 16 | 100 | 177 | 177 |
|  | 50 | 133 | 117 |
|  | 10 | 127 | 109 |
|  | 5 | 105 | 95 |
|  | 2.5 | 81 | 77 |
|  | 1 | 0 | 4 |
| 16 rerun | 100 | 186 | 114 |
|  | 50 | 102 | 108 |
|  | 25 | 78 | 71 |
|  | 10 | 0 | 5 |
| 17 | 100 | 186 | 114 |
|  | 50 | 80 | 90 |
|  | 25 | 2 | 0 |
| 18 | 100 | 200 | 105 |
|  | 50 | 200 | 105 |
|  | 25 | 72 | 72 |
|  | 10 | 28 | 13 |
| 19 | 100 | 186 | 114 |
|  | 50 | 116 | 104 |
|  | 25 | 62 | 71 |
|  | 10 | 8 | 14 |
| 20 | 100 | 52 | 62 |
|  | 100 | 51 | 52 |
|  | 50 | 23 | 14 |
| 21 | 100 | 97 | 107 |
|  | 100 | 111 | 128 |
|  | 50 | 16 | 5 |
| 22 | 100 | 200 | 105 |
|  | 50 | 200 | 105 |
|  | 25 | 10 | 0 |

-continued

| Example | Dose (mg/kg) | Initial Arrhythmia | Ventricular Tachycardia |
|---|---|---|---|
| 23 | 100 | 74 | 62 |
|  | 100 | 85 | 74 |
|  | 50 | 23 | 8 |
| 24 | 100 | 200 | 105 |
|  | 50 | 65 | 52 |
|  | 25 | 3 | 0 |
| 25 | 100 | 126 | 125 |
|  | 50 | 56 | 58 |
|  | 25 | 0 | 0 |
| 26 | 100 | 94 | 83 |
|  | 50 | 65 | 64 |
|  | 25 | 0 | 0 |
| 27 | 100 | 96 | 90 |
|  | 100 | 84 | 76 |
|  | 50 | 28 | 20 |
| 28 | 100 | 126 | 104 |
|  | 100 | 117 | 91 |
|  | 50 | 28 | 22 |
| 29 | 100 | 132 | 114 |
|  | 25 | 90 | 75 |
|  | 10 | 75 | 66 |
|  | 5 | 30 | 24 |
| 30 | 100 | 100 | 124 |
|  | 50 | 38 | 113 |
|  | 25 | 7 | 82 |
|  | 10 | 0 | 0 |
| 31 | 100 | 92 | 90 |
|  | 100 | 91 | 76 |
|  | 50 | 39 | 19 |
| 32 | 100 | Died | Died |
|  | 50 | 45 | 39 |
| 33 | 100 | 33 | 40 |
| 34 | 100 | 40 | 38 |
| 35 | 100 | 20 | 6 |
| 36 | 100 | 28 | 20 |
| 37 | 100 | 36 | 62 |
|  | 100 | 22 | 55 |
|  | 50 | 0 | 0 |
| 38 | 100 | Died | Died |
|  | 50 | 41 | 44 |
| 39 | 100 | 27 | 11 |
| 40 | 100 | 30 | 26 |
| Control (Lidocaine) | 50 | 113 | 95 |
| Control (Quinidine) | 50 | 108 | 89 |
| Control (Yohimbine • HCl) | 10 | 109 | 87 |
|  | 5 | 80 | 78 |
|  | 2.5 | 23 | 39 |

Additional compounds tested having structural formula I above and containing electronegative substituents such as $-NO_2$, $-SO_2$ or $-SO_3^-$, were inactive or tended to be less effective than Examples 1–40 above.

Additional compounds tested having structural formula I above but having poor solubility, e.g., less than about 3 mg/mL, in the carrier were inactive or tended to be less effective than Examples 1–40 above. This illustrates the importance that the compound be sufficiently soluble in the carrier to be efficacious.

The invention has been described in detail with particular reference to certain preferred embodiments thereof, but it will be understood that variations and modifications can be effected within the spirit and scope of the invention.

What is claimed is:

1. A method of treating arrythmias or inhibiting ventricular tachycardias in a mammalian subject in need thereof comprising administering to said subject an effective amount of a compound having the formula:

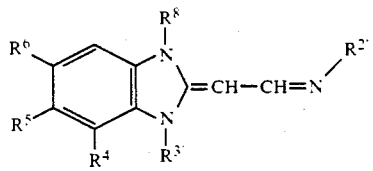

wherein $R^{2'}$ is t-butyl or phenyl;

$R^{3'}$ is ethyl or 2,2,2,-trifluoroethyl;

$R^4$, $R^5$ and $R^6$ are independently H, alkyl, aryl, alkylsulfonamido, arylsulfonamido, alkoxy, aryloxy, alkylthio, arylazo, alkenyl, cyano, halo, nitro, alkyl-CO-O-, alkyl-O-CO-, aryl-CO-O-, aryl-O-CO-, alkylcarbonylimino, alkyliminocarbonyl, arylcarbonylimino, aryliminocarbonyl, alkyl-CO-or aryl-CO-, or $R^4$ and $R^5$, or $R^5$ and $R^6$, or $R^4$, $R^5$ and $R^6$ taken together represent the atoms necessary to complete a fused carbocyclic ring group containing from 1 to 3 rings; and $R^8$ is alkyl, or aryl.

* * * * *